(12) United States Patent
Noguchi et al.

(10) Patent No.: US 10,307,381 B2
(45) Date of Patent: Jun. 4, 2019

(54) PATCH

(71) Applicant: HISAMITSU PHARMACEUTICAL CO., INC., Tosu-shi (JP)

(72) Inventors: Junji Noguchi, Tsukuba (JP); Eisuke Hatanaka, Tsukuba (JP); Hisakazu Kurita, Tosu (JP); Ryusuke Fudoji, Tsukuba (JP); Yasunari Michinaka, Tsukuba (JP)

(73) Assignee: HISAMITSU PHARMACEUTICAL CO., INC., Tosu-shi (JP)

( * ) Notice: Subject to any disclaimer, the term of this patent is extended or adjusted under 35 U.S.C. 154(b) by 0 days.

(21) Appl. No.: 15/518,847

(22) PCT Filed: Oct. 13, 2015

(86) PCT No.: PCT/JP2015/078940
§ 371 (c)(1),
(2) Date: Apr. 13, 2017

(87) PCT Pub. No.: WO2016/060122
PCT Pub. Date: Apr. 21, 2016

(65) Prior Publication Data
US 2017/0224630 A1    Aug. 10, 2017

(30) Foreign Application Priority Data

Oct. 14, 2014 (JP) .................. 2014-209824

(51) Int. Cl.
| | | |
|---|---|---|
| *A61K 31/485* | (2006.01) |
| *A61K 9/70* | (2006.01) |
| *A61K 47/10* | (2017.01) |
| *A61K 31/00* | (2006.01) |
| *A61K 47/06* | (2006.01) |
| *C08F 226/02* | (2006.01) |
| *C08F 226/10* | (2006.01) |
| *C08K 5/092* | (2006.01) |

(52) U.S. Cl.
CPC .......... *A61K 9/7053* (2013.01); *A61K 9/7061* (2013.01); *A61K 31/00* (2013.01); *A61K 31/485* (2013.01); *A61K 47/06* (2013.01); *A61K 47/10* (2013.01); *C08F 226/02* (2013.01); *C08F 226/10* (2013.01); *C08K 5/092* (2013.01)

(58) Field of Classification Search
CPC ..... A61L 2420/04; A61K 9/2806; A61K 9/70; A61K 9/5078; A61K 31/485
See application file for complete search history.

(56) References Cited

U.S. PATENT DOCUMENTS

| | | |
|---|---|---|
| 3,775,414 A | 11/1973 | Monkovic et al. |
| 3,819,635 A | 6/1974 | Pachter et al. |
| 4,626,539 A | 12/1986 | Aungst et al. |
| 2008/0226697 A1 | 9/2008 | Yamaguchi et al. |
| 2009/0004255 A1* | 1/2009 | Uchida ............... A61K 9/7053 424/447 |

FOREIGN PATENT DOCUMENTS

| | | |
|---|---|---|
| JP | 61-83116 A | 4/1986 |
| WO | 2005/102393 A1 | 11/2005 |

OTHER PUBLICATIONS

Michal Svozil, et al., "In Vitro Studies on Transdermal Permeation of Butorphanol," Drug Development and Industrial Pharmacy, Informa Healthcare, vol. 33, 2007, pp. 559-567.
International Search Report dated Jan. 12, 2016 in PCT/JP2015/078940 filed Oct. 13, 2015.

* cited by examiner

*Primary Examiner* — Tracy Liu
(74) *Attorney, Agent, or Firm* — Oblon, McClelland, Maier & Neustadt, L.L.P.

(57) ABSTRACT

A patch including: a support; and an adhesive layer disposed on at least one surface of the support, in which the adhesive layer includes: at least one selected from the group consisting of butorphanol and pharmaceutically acceptable salts thereof; a higher aliphatic alcohol; and a non-cross-linking polyvinylpyrrolidone that does not contain vinyl acetate as a constituent monomer thereof.

9 Claims, 3 Drawing Sheets

[Fig. 1]
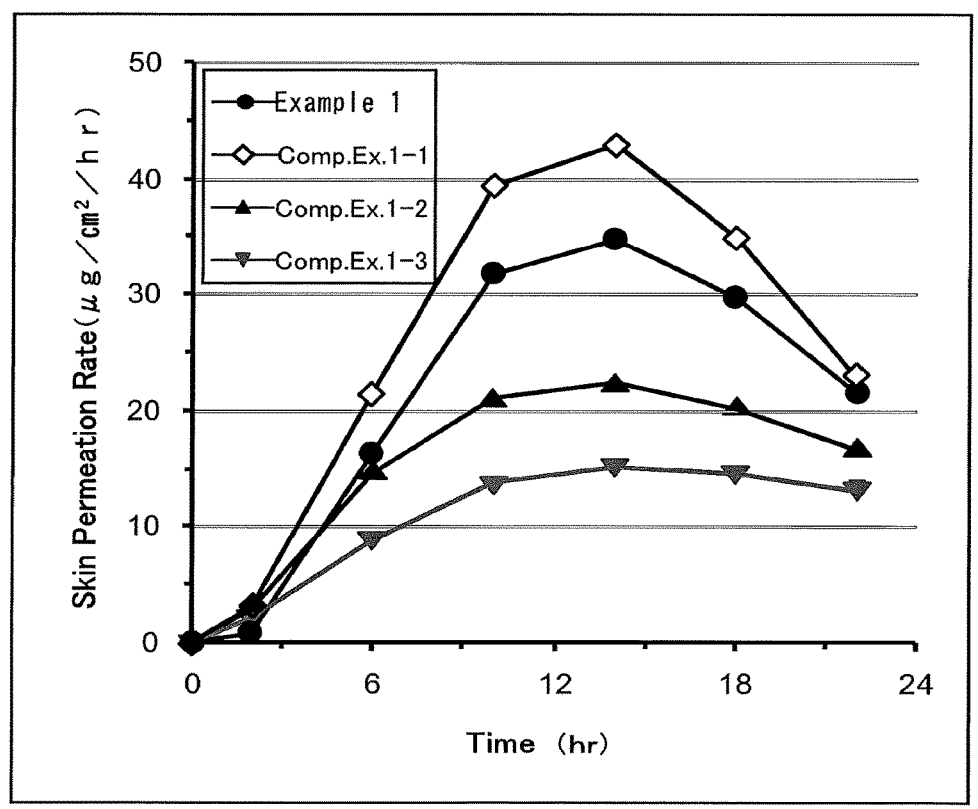

[Fig. 2]
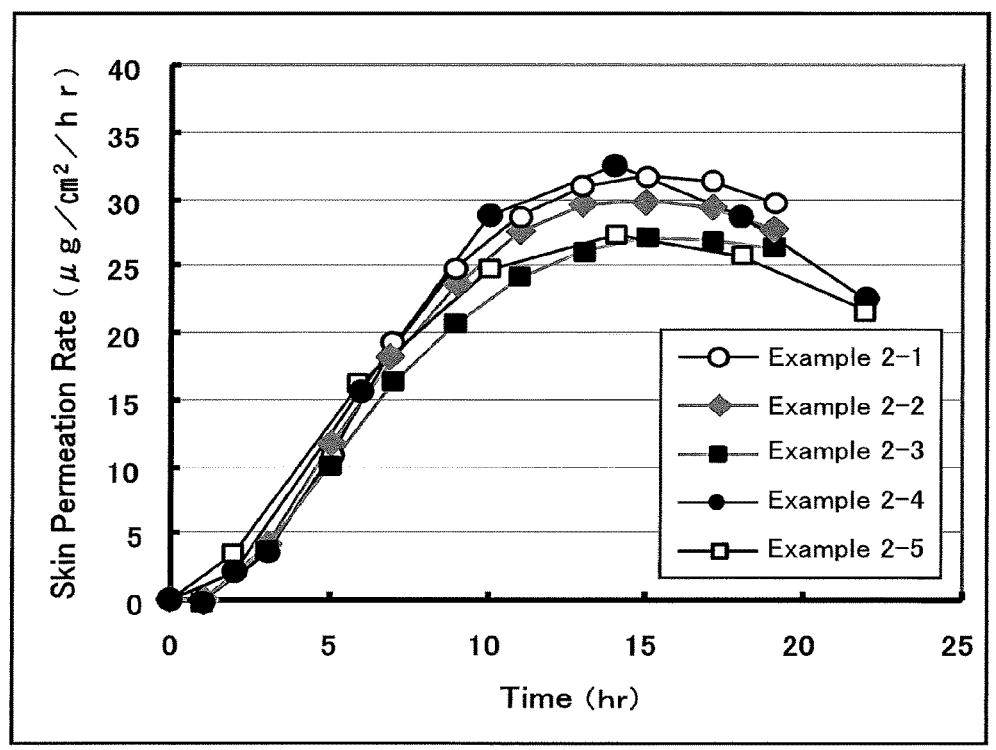

[Fig. 3]
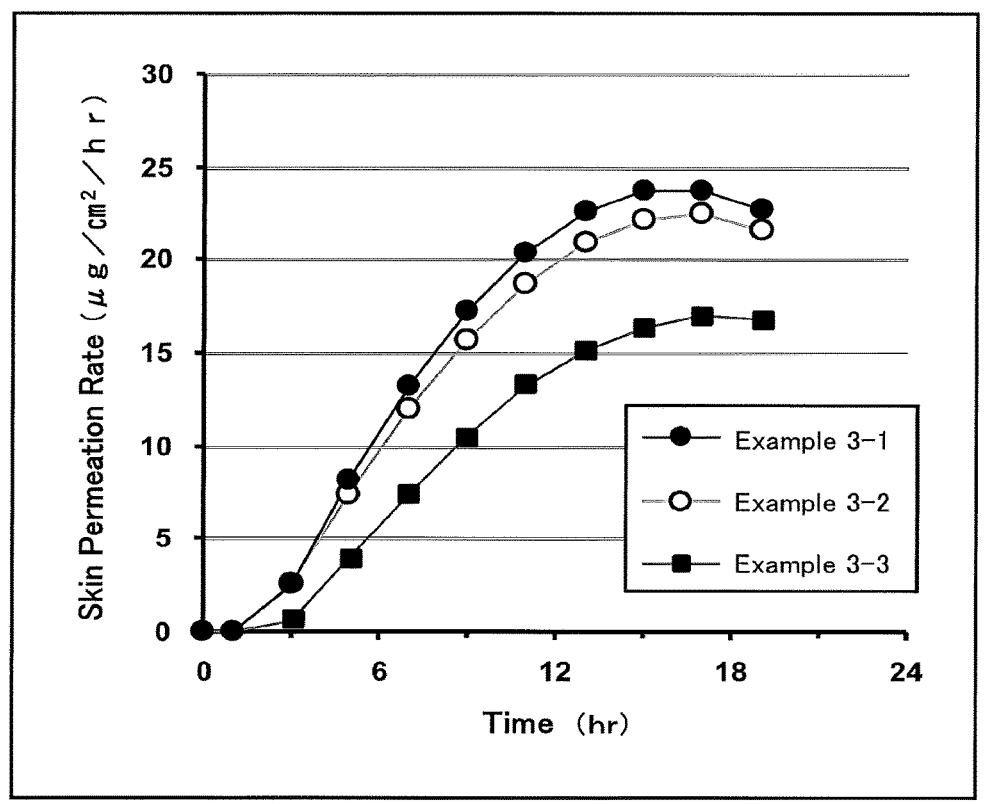

PATCH

TECHNICAL FIELD

The present invention relates to a patch, and more particularly relates to a patch containing at least one selected from the group consisting of butorphanol and salts thereof.

BACKGROUND ART

Butorphanol is a drug that is classified into an opioid-based analgesic and has a molecular structure of morphinan skeleton. An injection containing butorphanol tartrate for postoperative analgesia has been utilized. As such butorphanol, N-cyclobutylmethyl-3,14-dihydroxymorphinan is disclosed in U.S. Pat. No. 3,775,414 (PTL 1) and U.S. Pat. No. 3,819,635 (PTL 2), for example.

In addition, an in vitro study on transdermal permeation of butorphanol has been reported in M. Svozil et al., Drug. Dev. Ind. Pharm., 33(5), 559-67 (2007) (NPL 1). NPL 1 discloses that butorphanol is an effective drug as a drug for transdermal therapeutic system, and that transkarbam 12, laurocapram (which is the same as AZONE (trade mark)), and isopropylmyristate have been studied as transdermal absorption enhancers, and transkarbam is particularly suitable.

Meanwhile, International Publication No. 2005/102393 (PTL 3) discloses a pressure-sensitive adhesive composition for transdermal absorption, containing a drug, a transdermal absorption enhancer, and a polyvinylpyrrolidone. PTL 3 states that the drug is not particularly limited as long as the drug is one used in general, and illustrates and lists 32 drug classes, such as hypnotic and sedative agents, antipyretic, anti-inflammatory, and analgesic agents, steroidal anti-inflammatory agents, excitants and stimulants, neuropsychiatric agents, and agents for urinary organs, and a large number of drugs over a wide variety for each of these drug classes. As one of the antipyretic, anti-inflammatory, and analgesic agents among them, butorphanol tartrate is given. In addition, as the transdermal absorption enhancer, a wide variety of compounds are illustrated, such as carboxylic acids having 2 to 7 carbon atoms, fatty acids having 6 to 20 carbon chains, fatty acid esters or ethers, aromatic organic acids, aromatic alcohols, aromatic organic acid esters or ethers, lactylic esters, acetic esters, monoterpene-based compounds, sesquiterpene-based compounds, and aliphatic alcohols are given as one kind of them. However, PTL 3 substantially describes no pharmaceutical preparation containing butorphanol, and neither discloses nor suggests at all a combination of butorphanol and a particular transdermal absorption enhancer, or the skin permeability and crystal precipitation of butorphanol.

CITATION LIST

Patent Literatures

[PTL 1] U.S. Pat. No. 3,775,414
[PTL 2] U.S. Pat. No. 3,819,635
[PTL 3] International Publication No. 2005/102393

Non Patent Literature

[NPL 1] M. Svozil et al., Drug. Dev. Ind. Pharm., 33(5), 559-67 (2007)

SUMMARY OF INVENTION

Technical Problem

The present inventors have studied patches containing butorphanol as drugs, and found the following problem. Specifically, the present inventors have found that if an adhesive layer contains a higher aliphatic alcohol, the transdermal absorbability of butorphanol as the drug can be enhanced, with which however, crystals of the drug precipitate with time, and the precipitation lowers the skin permeability of the drug.

The present invention has been made in view of the above-described problem, and has an object to provide a patch in which the crystal precipitation of butorphanol is sufficiently suppressed and which is excellent in skin permeability of butorphanol.

Solution to Problem

As a result of earnest studies to achieve the above-described object, the present inventions have found that by causing, in a patch comprising: a support; and an adhesive layer disposed on at least one surface of the support, the adhesive layer to contain butorphanol as a drug, and to also contain a non-cross-linking polyvinylpyrrolidone that does not contain vinyl acetate as a constituent monomer thereof and a higher aliphatic alcohol in combination, it is surprisingly possible to obtain a patch in which the precipitation of crystals of butorphanol is sufficiently suppressed and which exhibits an excellent skin permeability, and have completed the present invention.

Specifically, the patch of the present invention is a patch comprising: a support and an adhesive layer disposed on at least one surface of the support, wherein the adhesive layer comprises: at least one selected from the group consisting of butorphanol and pharmaceutically acceptable salts thereof; a higher aliphatic alcohol; and a non-cross-linking polyvinylpyrrolidone that does not contain vinyl acetate as a constituent monomer thereof.

In the patch of the present invention, the higher aliphatic alcohol is preferably at least one selected from the group consisting of isostearyl alcohol, octyldodecanol, and oleyl alcohol.

In addition, in the patch of the present invention, a content ratio between the at least one selected from the group consisting of butorphanol and pharmaceutically acceptable salts thereof and the polyvinylpyrrolidone is preferably in a range of 1:0.8 to 2.5 in mass ratio ([the at least one selected from the group consisting of butorphanol and pharmaceutically acceptable salts thereof converted as a free form]:[the polyvinylpyrrolidone]).

Moreover, the patch of the present invention preferably further comprises styrene-isoprene-styrene block copolymer in the adhesive layer.

In addition, in the patch of the present invention, a content of the at least one selected from the group consisting of butorphanol and pharmaceutically acceptable salts thereof (in terms of a mass of a tartaric acid addition salt) is preferably 4 to 20% by mass, based on a total mass of the adhesive layer.

Advantageous Effects of Invention

According to the present invention, it is possible to provide a patch in which the precipitation of crystals of butorphanol is sufficiently suppressed and which is excellent in skin permeability of butorphanol.

BRIEF DESCRIPTION OF DRAWINGS

FIG. 1 is a graph showing results of a hairless mouse skin permeation test on patches obtained in Example 1 and Comparative Examples 1-1 to 1-3.

FIG. 2 is a graph showing results of a hairless mouse skin permeation test on patches obtained in Examples 2-1 to 2-5.

FIG. 3 is a graph showing results of a hairless mouse skin permeation test on patches obtained in Examples 3-1 to 3-3.

DESCRIPTION OF EMBODIMENTS

Hereinafter, the present invention will be described in detail by preferred embodiments thereof.
[Patch]

First, a patch of the present invention will be described. Specifically, the patch of the present invention comprises a support and an adhesive layer disposed on at least one surface of the support, wherein the adhesive layer comprises: at least one selected from the group consisting of butorphanol and pharmaceutically acceptable salts thereof (hereinafter, sometimes, collectively called a "drug", or simply "butorphanol"); a higher aliphatic alcohol; and a non-cross-linking polyvinylpyrrolidone that does not contain vinyl acetate as a constituent monomer thereof.
(Support)

It is necessary for the patch of the present invention to comprise a support.

Such a support used for the patch of the present invention is not particularly limited, and a support known as a support for patches can be employed as appropriate. The usable material of the support includes, for example, polyolefins such as polyethylene and polypropylene, ethylene-vinyl acetate copolymers, vinyl acetate-vinyl chloride copolymers, polyvinyl chlorides, polyamides such as nylon, polyesters such as polyethylene terephthalate (PET), polybutylene terephthalate and polyethylene naphthalate, synthetic resins such as cellulose derivatives and polyurethane, metals such as aluminum, and the like. Note that from the viewpoints of the non-adsorbability for the drug, the non-transmittability for the drug, and the like, polyesters and polyethylene terephthalate are preferable. In addition, the usable form of the support includes, for example, a film, a sheet, a sheet-shaped porous body, a sheet-shaped foam, fabrics such as woven fabric, a knitted fabric (knit), and a nonwoven fabric, a foil, a laminate of these, and the like.
(Adhesive Layer)

It is necessary for the patch of the present invention to comprise an adhesive layer disposed on at least one surface of the support. In addition, such an adhesive layer contains at least one selected from the group consisting of butorphanol and pharmaceutically acceptable salts thereof.
<Butorphanol and Pharmaceutically Acceptable Salts Thereof>

It is necessary for the patch of the present invention to contain at least one selected from the group consisting of butorphanol and pharmaceutically acceptable salts thereof, which will be described below, in the adhesive layer.

Here, the butorphanol refers to 17-(cyclobutylmethyl) morphinan-3,14-diol, which is expressed by a molecular formula of $C_{21}H_{29}NO_2$. The butorphanol is one of drugs classified into opioid-based analgesics and having molecular structures of morphinan skeleton.

In the present invention, the form of butorphanol contained as the drug (an effective ingredient) may be a free form or pharmaceutically acceptable acid addition salts of butorphanol, may be one or a mixture of two or more thereof. Among these, the form of butorphanol according to the present invention is preferably a pharmaceutically acceptable acid addition salt of butorphanol from the viewpoint that this tends to improve the stability of the drug.

Such pharmaceutically acceptable acid addition salts of butorphanol specifically include addition salts with all the inorganic and organic acids, and includes addition salts with acids selected from hydrochloric acid, sulfuric acid, nitric acid, phosphoric acid, phosphorouc acid, hydrobromic acid, maleic acid, malic acid, ascorbic acid, tartaric acid, lauric acid, stearic acid, palmitic acid, oleic acid, myristic acid, lauryl sulfuric acid, linolenic acid, and the like. Among these, an addition salt with tartaric acid as expressed by the following structural formula is preferable:

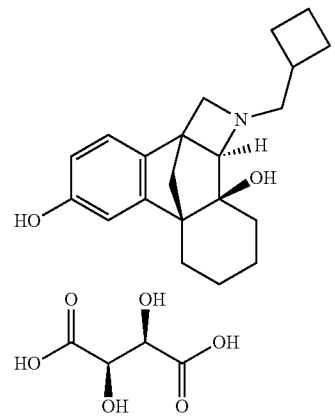

[Chem. 1]

In the patch of the present invention, when the at least one selected from the group consisting of butorphanol and pharmaceutically acceptable salts thereof as the drug is blended with an adhesive base agent, a part of the drug is dissolved into the adhesive base agent, so that the drug is allowed to permeate from the adhesive layer into a skin, providing therapeutic effects to the living organism.

In the patch of the present invention, the total content of the at least one selected from the group consisting of butorphanol and pharmaceutically acceptable salts thereof (in terms of the mass of the tartaric acid addition salt) is preferably 4 to 20% by mass, and more preferably 7 to 11% by mass, based on the total mass in the adhesive layer. If the content is lower than the lower limit, the skin permeability of butorphanol as the drug is insufficient, so that a sufficient amount of butorphanol for treatment is unlikely to be supplied to the skin. On the other hand, if the content exceeds the upper limit, it is difficult to maintain the drug in a dissolved state in the adhesive layer, so that crystals of butorphanol precipitate, which tend to lower the adhesive force of the adhesive layer, lower the skin permeability of the drug, and further impair the performance of the patch such as the uniformity of the content.

In other words, if the content of the at least one selected from the group consisting of butorphanol and pharmaceutically acceptable salts thereof as the drug is in the range of 4 to 20% by mass (more preferably 7 to 11% by mass), an appropriate amount of the drug can be dissolved in the adhesive base agent, and also a favorable skin permeation rate of the drug for treatment tends to be exhibited.

<Higher Aliphatic Alcohol>

It is necessary for the patch of the present invention to contain a higher aliphatic alcohol in the adhesive layer. Blending a higher aliphatic alcohol in the adhesive layer makes it possible to improve (promote) the transdermal absorbability of butorphanol contained in the adhesive layer.

Such a higher aliphatic alcohol used in the patch of the present invention is preferably an aliphatic alcohol having 12 to 20 carbon atoms, and includes, for example, lauryl alcohol, myristyl alcohol (1-tetradecanol), cetyl alcohol (cetanol), stearyl alcohol (1-octadecanol), isostearyl alcohol (16-methylheptadecen-1-ol), oleyl alcohol (cis-9-octadecen-1-ol), linolenyl alcohol, arachyl alcohol (arachidyl alcohol, 1-eicosanol), octyldodecanol, and mixtures of these. Note that, as such a higher aliphatic alcohol, aliphatic alcohols having less carbon atoms than lauryl alcohol (12 carbon atoms) are not preferable because they have relatively strong skin irritation. On the other hand, aliphatic alcohols having more carbon atoms than arachyl alcohol (20 carbon atoms) are not preferable because they form waxy lumps in the drug.

Note that, such a higher aliphatic alcohol is further preferably at least one selected from the group consisting of isostearyl alcohol, octyldodecanol, and oleyl alcohol, from the viewpoint that the skin permeability of the drug tends to be further improved. Moreover, such a higher aliphatic alcohol is particularly preferably oleyl alcohol.

In the patch of the present invention, the content of such a higher aliphatic alcohol is preferably 3 to 25% by mass, and more preferably 4 to 20% by mass, based on the total mass in the adhesive layer. If the content is less than the lower limit, the skin permeability of butorphanol tends to be insufficient. On the other hand, if the content exceeds the upper limit, crystals derived from butorphanol tend to precipitate with time, thus lowering the adhesive force of the adhesive layer.

<Polyvinylpyrrolidone>

It is necessary for the patch of the present invention to contain a non-cross-linking polyvinylpyrrolidone that does not contain vinyl acetate as a constituent monomer thereof in the adhesive layer (hereinafter, sometimes called a "polyvinylpyrrolidone of the present invention"). Containing the polyvinylpyrrolidone of the present invention in the adhesive layer makes it possible to suppress precipitation of crystals derived from butorphanol contained in the adhesive layer.

Such a polyvinylpyrrolidone (abbreviated as "PVP" or called also povidone) of the present invention used in the patch of the present invention is not particularly limited as long as the polyvinylpyrrolidone is a non-cross-linking polyvinylpyrrolidone that does not contain vinyl acetate as a constituent monomer thereof, which functions as a crystal precipitation inhibitor for butorphanol. Specifically, such a polyvinylpyrrolidone is preferably a polyvinylpyrrolidone having a K value in a range of 10 to 120, more preferably a polyvinylpyrrolidone having a K value of 10 to 100, and further preferably a polyvinylpyrrolidone having a K value in a range of 10 to 90, from the viewpoint that the precipitation of crystals derived from butorphanol contained in the adhesive layer can be more suppressed. Among such polyvinylpyrrolidones, at least one selected from the group consisting of polyvinylpyrrolidone K12, polyvinylpyrrolidone K15, polyvinylpyrrolidone K17, polyvinylpyrrolidone K25, polyvinylpyrrolidone K29/32, polyvinylpyrrolidone K30, polyvinylpyrrolidone K60, and polyvinylpyrrolidone K90 is particularly preferable.

Note that the use of a polyvinylpyrrolidone having a K value in a range of 10 to 30 tends to more suppress the precipitation of crystals derived from butorphanol. In addition, the polyvinylpyrrolidone may be one that contains a pyrogenic substance or may be one from which a pyrogenic substance has been removed. Such a K value is calculated by applying the viscosity in an aqueous solution to the Fikentscher's formula. A method of measuring a K value is carried out according to the description of povidone in Japanese Pharmacopoeia.

In addition, the concentration of the polyvinylpyrrolidone in the adhesive layer is not particularly limited as long as the concentration makes it possible to suppress crystals derived from butorphanol. However, it is preferable to blend the polyvinylpyrrolidone in a concentration similar to that of butorphanol. Accordingly, in the patch of the present invention, the content of the polyvinylpyrrolidone is preferably 4 to 20% by mass, and more preferably 7 to 11% by mass, based on the total mass in the adhesive layer. If the content is less than the lower limit, crystals of the drug tend to easily precipitate. On the other hand, if the content exceeds the upper limit, the skin permeability of the drug tends to be lowered.

Further, as such patch of the present invention, the content ratio between the at least one selected from the group consisting of butorphanol and pharmaceutically acceptable salts thereof and the polyvinylpyrrolidone is preferably in a range of 1:0.8 to 2.5 in mass ratio ([the at least one selected from the group consisting of butorphanol and pharmaceutically acceptable salts thereof converted as a free form]: [the polyvinylpyrrolidone]). The content ratio in such a range tends to further improve the skin permeability of the butorphanol and also to effectively suppress the precipitation of crystals derived from butorphanol.

<Adhesive Base Agent>

The patch of the present invention preferably contains an adhesive base agent in the adhesive layer, and normally contains an adhesive base agent. Such an adhesive base agent in the adhesive layer is not particularly limited as long as the adhesive base agent can be a base agent for the adhesive layer. However, the adhesive base agent is preferably an adhesive base agent having adhesiveness at a temperature where the patch is applied (preferably 0° C. to 50° C., more preferably 10° C. to 40° C., and further preferably 15° C. to 40° C.). Moreover, such an adhesive base agent is more preferably one that is excellent in skin permeability of butorphanol and/or capable of suppressing the precipitation of crystals of butorphanol.

Such an adhesive base agent may be a polymer made of a hydrocarbon, and further may be a polymer containing oxygen and/or nitrogen in molecule. Moreover, the adhesive base agent may not contain water.

Specifically, such an adhesive base agent includes a rubber-based adhesive base agent, an adhesive base agent made of an acrylic acid ester polymer, a silicone adhesive base agent, a urethane adhesive base agent, combinations of these, and the like.

The rubber-based adhesive base agent may be natural rubber, or as a synthetic rubber, styrene-isoprene-styrene block copolymer (SIS), styrene-butadiene-styrene block copolymer, styrene-isoprene copolymer, styrene-butadiene copolymer, polyisoprene, polyisobutylene (PIB), polybutadiene, and combinations of these may be used. When a rubber-based adhesive base agent is used as such an adhesive base agent, the content of the rubber-based adhesive base agent is preferably 10 to 95% by mass, and more preferably 20 to 90% by mass, based on the total mass in the adhesive layer.

Regarding the adhesive base agent made of an acrylic acid ester polymer, the acrylic adhesive base agent is not particularly limited as long as the acrylic adhesive base agent is obtained by containing and polymerizing at least one of (meth)acryl acids (esters) such as acrylic acid, 2-ethylhexyl acrylate, methyl acrylate, butyl acrylate, hydroxyethyl acrylate, or 2-ethylhexyl methacrylate as a monomer. Such an acrylic adhesive base agent includes 2-ethylhexyl acrylate-vinyl acetate copolymer, 2-ethylhexyl acrylate-vinyl acetate-acrylic acid copolymer, 2-ethylhexyl acrylate-vinyl acetate-hydroxyethyl acrylate copolymer, 2-ethylhexyl acrylate-vinyl acetate-hydroxyethyl acrylate-acrylic acid copolymer, 2-ethylhexyl acrylate-2-ethylhexyl methacrylate-dodecyl methacrylate copolymer, and the like, and particularly, 2-ethylhexyl acrylate-vinyl acetate copolymer, and 2-ethylhexyl acrylate-vinyl acetate-acrylic acid copolymer are preferable. One of these acrylic adhesive base agents may be used alone, or two or more of them may be used in combination. When an adhesive base agent made of an acrylic acid ester polymer is used as such an adhesive base agent, the content of the adhesive base agent made of the acrylic acid ester polymer is preferably 10 to 95% by mass, and more preferably 30 to 90% by mass, based on the total mass in the adhesive layer.

Among these adhesive agents, styrene-isoprene-styrene block copolymer (SIS) is preferable, and a mixture of styrene-isoprene-styrene block copolymer (SIS) and polyisobutylene (PIB) is more preferable, from the viewpoint that the skin permeability of butorphanol tends to be more improved.

<Other Additives>

The patch of the present invention may further contain a desalting agent, a tackifier resin, a plasticizer, a stabilizer, a solubilizer for the drug, and the like in the adhesive layer, in addition to the above-described components The desalting agent is blended to convert all or a part of the basic drug into a free base (educt) state. Such desalting agent is not particularly limited, but a basic substance is suitable when a drug generated from an acid addition salt is used as the drug. From the viewpoint of completely desalting the acid addition salt of the drug, sodium acetate, sodium hydroxide, potassium hydroxide, magnesium hydroxide, and the like are given. Among these, sodium acetate and sodium hydroxide are particularly preferable. Note that, as the content of such a desalting agent, the desalting agent is blended preferably in an equivalent amount in a range of 0.5 to 4, and more preferably in an equivalent amount in a range of 0.5 to 3, relative to the acid-base equivalent amount of the drug, from the viewpoint of not decomposing the drug with an excessive amount of the desalting agent. The blending may be conducted at once, or may be conducted at several separate stages, in the manufacturing process.

The tackifier is blended to enhance the adhesiveness of the adhesive layer. Such a tackifier includes, for example, rosin-based resins such as "Ester Gum (trade name, Arakawa Chemical Industries, Ltd.)", "Hariester (trade name, Harima Chemicals, Inc.)", "Pentalyn (trade name, Eastman Chemical Company)", and "Foral (trade name, Eastman Chemical Company)", terpene-based resins such as "YS Resin (trade name, Yasuhara Chemical Co., Ltd.)" and "Piccolyte (trade name, Loos & Dilworth Inc.), and petroleum resins such as "Arkon (trade name, Arakawa Chemical Industries, Ltd.)", "Regalrez (trade name, Eastman Chemical Company)", "Piccolastic (trade name, Eastman Chemical Company)", "Escorez (trade name, Exxon Mobil Corporation)", "Wingtack (trade name, Goodyear Tire & Rubber Company)", and "Quintone (trade name, Zeon Corporation)", phenolic resins, and xylene-based resins.

These tackifiers may be used alone or may be used in combination of two or more of them. Note that the content of such a tackifier is preferably 10 to 90% by mass, and more preferably 20 to 60% by mass, based on the total mass in the adhesive layer, from the viewpoint of improving the adhesiveness of the patch and/or reducing local irritation at the time of peeling off.

The plasticizer is blended to adjust the adhesiveness of the adhesive layer, the fluidity during manufacture of the adhesive layer, the transdermal absorbability of the drug, and the like. Such a plasticizer includes, for example, petroleum-based oils such as paraffinic process oils, naphthenic process oils, and aromatic process oils; squalane, squalene; vegetable-based oils such as olive oil, camellia oil, castor oil, tall oil, and peanut oil, dibasic esters such as dibutyl phthalate and dioctyl phthalate, liquid rubbers such as polybutene and liquid isoprene rubber, diethylene glycol, polyethylene glycol, propylene glycol, dipropylene glycol, and the like. These may be used alone or may be used in combination of two or more of them. Note that among these plasticizers, liquid paraffin and/or liquid polybutene are preferably used.

The stabilizer is blended to enhance the stability of the adhesive layer and/or the drug. As such a stabilizer, for example, an antioxidant, an ultraviolet absorber, a metal chloride, and the like may be used as appropriate. The antioxidant includes, for example, tocopherols and ester derivatives thereof, ascorbic acid, ascorbic acid stearate, nordihydroguaiaretic acid, dibutylhydroxytoluene (hereinafter, abbreviated as BHT), butylatedhydroxyanisole. Among these, BHT is preferably used. In addition, the ultraviolet absorber includes p-aminobenzoic acid derivatives, anthranilic acid derivatives, salicylic acid derivatives, coumarin derivatives, for example, amino acid-based compounds, imidazoline derivatives, pyrimidine derivatives, dioxane derivatives, dibenzoylmethane derivatives, and the like.

The solubilizer for the drug is blended to promote the dissolution of the drug. Such a solubilizer includes, for example, organic acids such as acetic acid, aliphatic alcohols, and surfactants. Among these, organic acids and aliphatic alcohols are preferable.

As additives other than those described above, fillers, preservatives, and the like are further used as appropriate.

The filler is blended mainly to adjust the adhesive force of the adhesive layer. Such a filler includes, for example, aluminum hydroxide, calcium carbonate, magnesium carbonate; silicate such as aluminum silicate and magnesium silicate; silicic acid, barium sulfate, calcium sulfate, calcium zincate, zinc oxide, and titanium oxide.

The preservative is blended to improve the preservation stability of the drug. Such a preservative includes, for example, disodium edetate, tetrasodium edetate, ethyl paraoxybenzoate, propyl paraoxybenzoate, butyl paraoxybenzoate, and the like.

(Patch)

The patch of the present invention is a patch comprising: the support; and the adhesive layer provided on at least one surface of the support.

The thickness of the adhesive layer in the patch of the present invention as described above (exclusive of the thicknesses of the support and the release liner) is not particularly limited, but is preferably 30 to 300 µm. The thickness in this range makes it possible to continually (durably) administer the drug, and also improve the adhesiveness, the cohesive force, the attachment continuity, the pain during peeling off, and the like.

In addition, the patch of the present invention as described above preferably comprises: the support; the adhesive layer provided on at least one surface of the support; and a release liner covering and protecting a surface of the adhesive layer which is not in contact with the support.

In the patch of the present invention as described above, the release liner is removed, the adhesive layer thus exposed is attached to a skin surface, and then, the butorphanol (salt) contained in the adhesive layer gradually permeates into the skin, and is absorbed in the living organism to provide physiological activities such as analgesia.

The release liner optionally comprised in the patch of the present invention is not particularly limited, and one known as a release liner for patches may be employed as appropriate. Materials of such a release liner include films made of polyolefins such as polyethylene and polypropylene, ethylene-vinyl acetate copolymers, vinyl acetate-vinyl chloride copolymers, polyvinyl chlorides, polyamides such as nylon, polyesters such as polyethylene terephthalate, synthetic resins such as cellulose derivatives and polyurethane, an aluminum foil, paper, and the like, and laminates and the like of these. In addition, release treatment such as silicone coating may be applied to the surface to facilitate the peeling.

[Method of Manufacturing Patch]

A method of manufacturing the patch of the present invention is not particularly limited, but for example, the patch of the present invention may be manufactured by the following method.

First, as raw materials of the adhesive layer, the drug, the higher aliphatic alcohol, the polyvinylpyrrolidone, and optionally selected various additives such as an adhesive base agent, a desalting agent, a tackifier resin, a plasticizer, a stabilizer, a solubilizer for the drug are prepared.

Next, the prepared raw materials of the adhesive layer are mixed with an appropriate amount of a solvent (for example toluene), followed by dissolution, dispersion, and the like, to obtain a mixed solution. Note that the raw materials of the adhesive layer may be mixed individually in a sequential order, or simultaneously.

Subsequently, the obtained mixed solution is applied in a uniform thickness to a release paper (a release liner) (for example, a polyethylene terephthalate (PET) film treated with silicone and a release liner made of polypropylene), and the solvent and the like are removed by drying to form the adhesive layer.

Next, a support (for example, a PET film or a polyester film) is stacked on the obtained adhesive layer, which is then cut into a desired size as appropriate to obtain the patch. Note that the obtained patch is enclosed in a storage package (for example, an aluminum-laminated bag) as necessary.

The preferred embodiment of the patch of the present invention has been described above; however, the present invention is not limited to the above-described embodiment.

EXAMPLE

Hereinafter, the present invention will be described more specifically based on Reference Examples, Examples, and Comparative Examples; however, the present invention is not limited to the following Examples.

Reference Example 1

First, 17.1% by mass of SIS block copolymer, 7.3% by mass of PIB, 43.9% by mass of a petroleum-based resin (a tackifier resin), 19.5% by mass of liquid paraffin, 5.0% by mass of butorphanol tartrate (in terms of the mass of tartaric acid addition salt), 2.2% by mass of anhydrous sodium acetate, and 5.0% by mass of oleyl alcohol as a transdermal absorption enhancer were measured out, and an appropriate amount of a solvent (anhydrous ethanol and toluene) was added, followed by mixing to obtain a raw material mixture solution of an adhesive layer. Then, the obtained raw material mixture solution of the adhesive layer was applied onto a release paper (a release sheet made of polyethylene terephthalate), and the solvent was removed by drying to form an adhesive layer (having a thickness of 100 g/m$^2$). Thereafter, a support (a PET film) was stacked on the adhesive layer, which was then cut into a predetermined size to obtain a reference patch according to Reference Example 1.

Next, an in vitro hairless mouse skin permeation test and a crystal precipitation evaluation test were conducted on the reference patch obtained in Reference Example 1 as described below, to evaluate the performance of the reference patch.

<In Vitro Hairless Mouse Skin Permeation Test>

First, the skin of the trunk of a hairless mouse was peeled off, and the fat was removed from the skin. Next, the reference patch was attached to the epidermis side, and then set in a Franz permeation test cell of a flow-through type such that the dermis side came into contact with a receptor solution. Subsequently, the cell was filled with the receptor solution (PBS), and a circulation water, which had been warmed such that the solution was kept at a temperature of 32° C., was circulated around the outer periphery of the cell, and the receptor solution was fed at a flow rate of approximately 2.5 mL/hr. Then, the solution was collected every 4 hours for 24 hours. The concentration of the butorphanol (salt) in the obtained solution was measured by high performance liquid chromatography, and the skin permeation amount (rate) of the butorphanol (salt) per hour was calculated. The maximum value of the skin permeation rate was taken as Jmax. In addition, the accumulated permeation amount of the drug until 24 hours was calculated.

<Crystal Precipitation Evaluation Test>

The prepared reference patch was packaged in an aluminum-laminate packaging material and was stored at room temperature. After 8 weeks, the surface of the adhesive layer of the reference patch was visually observed to check whether the crystal precipitation had occurred.

Regarding the obtained reference patches, the composition of the adhesive layer except the transdermal absorption enhancers is shown in Table 1, and the results of the conducted skin permeation test and crystal precipitation evaluation test are shown in Table 2 together with the transdermal absorption enhancers (each added in 5.0% by mass) in the adhesive layer.

TABLE 1

| Component | Content [% by mass] |
| --- | --- |
| SIS Block Copolymer | 17.1 |
| PIB | 7.3 |
| Petroleum-based Resin | 43.9 |
| Liquid Paraffin | 19.5 |
| Butorphanol Tartrate | 5.0 |
| Anhydrous Sodium Acetate | 2.2 |
| Absorption Enhancer (*) | 5.0 |
| Total [% by mass] | 100.0 |

TABLE 2

| | | Absorption Enhancer | Maximum Skin Permeation Rate (Jmax) [μg/cm²/hr] | Crystal Precipitation (Visually Checked) |
|---|---|---|---|---|
| Ref. Ex. 1 | Higher | Oleyl Alcohol | 13.0 | Entire Surface |
| Ref. Ex. 2 | Aliphatic | Isostearyl alcohol | 13.5 | Entire Surface |
| Ref. Ex. 3 | Alcohol | Octyldodecanol | 11.0 | Entire Surface |
| Ref. Ex. 4 | Higher | DES (Diethyl Sebacate) | 1.4 | No |
| Ref. Ex. 5 | Fatty Acid | Triacetin | 5.7 | No |
| Ref. Ex. 6 | Ester | DID (Diisopropyl Adipate) | 4.0 | No |
| Ref. Ex. 7 | | Triethyl Citrate | 4.6 | No |
| Ref. Ex. 8 | Surfactant | SML (Sorbitan Monolaurate) | 8.2 | In Spots |
| Ref. Ex. 9 | | Tween 80 (Polysorbate 80) | 4.4 | No |
| Ref. Ex. 10 | | LADA (Lauric Acid Diethanolamide) | 5.3 | No |
| Ref. Ex. 11 | | SMO (Sorbitan Monooleate) | 6.3 | In Spots |
| Ref. Ex. 12 | | STO (Sorbitan Trioleate) | 6.3 | In Spots |
| Ref. Ex. 13 | | POE OLEYL ETHER | 7.3 | No |
| Ref. Ex. 14 | Amine | MEA (Monoethanolamine) | 0.6 | No |
| Ref. Ex. 15 | | TEA (Triethanolamine) | 0.6 | No |
| Ref. Ex. 16 | Higher | Stearic Acid | 2.9 | In Spots |
| Ref. Ex. 17 | Fatty Acid | Isostearic Acid | 3.8 | In Spots |
| Ref. Ex. 18 | | Oleic Acid | 4.3 | In Spots |
| Ref. Ex. 19 | Alcohol | PG (Propylene Glycol) | 2.8 | No |
| Ref. Ex. 20 | (Polyhydric | Butylene Glycol | 2.7 | No |
| Ref. Ex. 21 | Alcohol) | DPG (Dipropylenc Glycol) | 3.4 | No |
| Ref. Ex. 22 | | PEG(Polyethylene Glycol) | 4.1 | No |
| Ref. Ex. 23 | | Glycerin | 3.6 | In Spots |
| Ref. Ex. 24 | | No | 4.8 | In Spots |

Reference Examples 2 to 23

Reference patches were obtained in the same manner as that of Reference Example 1 except that transdermal absorption enhancers shown in Table 2 were respectively used as transdermal absorption enhancers in place of oleyl alcohol (Reference Examples 2 to 23). The results of the skin permeation test conducted on the obtained reference patches of Reference Examples 2 to 23 are shown in Table 2.

Reference Example 24

A reference patch was obtained in the same manner as that of Reference Example 1 except that any transdermal absorption enhancer was not used (Reference Example 24). The result of the skin permeation test conducted on the obtained reference patch is shown in Table 2.

As is clear from the results shown in Tables 1 and 2, the reference patches using the higher aliphatic alcohols of Reference Examples 1 to 3 were confirmed to be excellent in skin permeability. Particularly, the reference patch of Reference Example 2 using oleyl alcohol as the transdermal absorption enhancer was confirmed to be more excellent in the effect of enhancing the skin permeability of the drug.

However, it was confirmed that in the reference patches of Reference Examples 1 to 3 containing higher aliphatic alcohols as the transdermal absorption enhancers, crystals derived from butorphanol precipitated with time on the entire surface of the patch, and the skin permeation rate of the drug was lowered to approximately half. Furthermore, the crystal precipitation was observed significantly in the higher aliphatic alcohols.

Example 1

First, 13.2% by mass of SIS block copolymer, 5.7% by mass of PIB, 34.1% by mass of a tackifier resin, 15.1% by mass of liquid paraffin and 9.0% by mass of a crystal precipitation inhibitor, 9.0% by mass of butorphanol tartrate, 3.9% by mass of anhydrous sodium acetate, and 10.0% by mass of oleyl alcohol as a transdermal absorption enhancer were measured out, and an appropriate amount of a solvent (anhydrous ethanol and toluene) was added, followed by mixing to obtain a raw material mixture solution of an adhesive layer. Then, the obtained raw material mixture solution of the adhesive layer was applied onto a release paper (a release sheet made of polyethylene terephthalate), and the solvent was removed by drying to form an adhesive layer (having a thickness of 100 g/m²). Thereafter, a support (a PET film) was stacked on the adhesive layer, which was then cut into a predetermined size to obtain a patch according to Example 1.

Next, the in vitro hairless mouse skin permeation test was conducted on the patch obtained in Example 1 in the same manner as that of Reference Example 1. Note that the rate of utilization (%) of the drug was calculated in accordance with the following equation:

The rate of utilization (%)={(the accumulated skin permeation amount of the drug for 24 hours per 1 cm² of the patch)/(the content of the drug per 1 cm² of the patch)}×100.

The preparation having a large value of the maximum value of skin permeation rate and/or the accumulated skin permeation amount is confirmed to be excellent in skin permeability of the drug.

In addition, the crystal precipitation evaluation test was conducted as described below, to evaluate the performance of the patch.

<Crystal Precipitation Evaluation Test>

The prepared patch was packaged in an aluminum-laminate packaging material and stored in a chamber having a temperature of 60° C. and a humidity of 75%. After 2 weeks, the surface of the adhesive layer of the patch was visually observed to check whether the crystal precipitation had occurred.

Regarding the obtained patches, the composition of the adhesive agent is shown in Tables 3 and 4, the result of the conducted skin permeation test is shown in Table 5 and FIG. 1, and the result of the conducted crystal precipitation evaluation test is shown in Table 6.

TABLE 3

Composition of Adhesive

| Component | Pharmaceutical Preparation 1-1 Content [% by mass] | Pharmaceutical Preparation 1-2 Content [% by mass] | Pharmaceutical Preparation 1-3 Content [% by mass] |
|---|---|---|---|
| SIS Block Copolymer | 13.2 | 13.0 | 13.4 |
| PIB | 5.7 | 13.0 | 13.4 |
| Tackifier Resin | 34.1 | 30.1 | 30.9 |
| Liquid Paraffin | 15.1 | 16.0 | 16.4 |
| Butorphanol Tartrate | 9.0 | 9.0 | 9.0 |
| Anhydrous Sodium Acetate | 3.9 | 3.9 | 3.9 |
| Oleyl Alcohol | 10.0 | 10.0 | 10.0 |
| Crystal Precipitation Inhibitor | 9.0 | 5.0 | 3.0 |
| Total [% by mass] | 100.0 | 100.0 | 100.0 |

TABLE 4

| | Adhesive | Crystal Precipitation Inhibitor |
|---|---|---|
| Example 1 | Pharmaceutical Preparation 1-1 | Polyvinylpyrrolidone (PVP K-29/32) |
| Comparative Example 1-1 | Pharmaceutical Preparation 1-1 | Cross-linking Polyvinylpyrrolidone (cPVP) |
| Comparative Example 1-2 | Pharmaceutical Preparation 1-1 | Polyvinylpyrrolidone-Vinyl Acetate Copolymer (PVP VA-64) |
| Comparative Example 1-3 | Pharmaceutical Preparation 1-1 | Aminoalkyl Methacrylate Copolymer E |
| Comparative Example 1-4 | Pharmaceutical Preparation 1-2 | Hydroxypropyl Cellulose (HPC SL) |
| Comparative Example 1-5 | Pharmaceutical Preparation 1-3 | Hydroxypropyl Cellulose (HPC SSL) |
| Comparative Example 1-6 | Pharmaceutical Preparation 1-2 | Hydroxypropyl Methylcellulose (METOLOSE 100SR) |
| Comparative Example 1-7 | Pharmaceutical Preparation 1-2 | Hydroxypropyl Methylcellulose (METOLOSE 4000SR) |
| Comparative Example 1-8 | Pharmaceutical Preparation 1-3 | Hydroxypropyl Methylcellulose (METOLOSE 15000SR) |
| Comparative Example 1-9 | Pharmaceutical Preparation 1-2 | Methacrylic Acid Copolymer (Eudragit L100) |
| Comparative Example 1-10 | Pharmaceutical Preparation 1-3 | Silicon Dioxide |

TABLE 5

| | Maximum Skin Permeation Rate (Jmax) [µg/cm²/hr] | Accumulated Skin Permeation Amount [µg/cm²/24 hr] | Rate of Utilization [%] |
|---|---|---|---|
| Example 1 | 35 | 538 | 60 |
| Comparative Example 1-1 | 43 | 657 | 73 |
| Comparative Example 1-2 | 22 | 390 | 43 |
| Comparative Example 1-3 | 15 | 269 | 30 |

TABLE 6

| | Crystal Precipitation (Visually Checked) |
|---|---|
| Example 1 | No |
| Comparative Example 1-1 | Yes |
| Comparative Example 1-2 | Yes |
| Comparative Example 1-3 | Yes |
| Comparative Example 1-4 | Yes |
| Comparative Example 1-5 | Yes |
| Comparative Example 1-6 | Yes |
| Comparative Example 1-7 | Yes |
| Comparative Example 1-8 | Yes |
| Comparative Example 1-9 | Yes |
| Comparative Example 1-10 | Yes |

Comparative Examples 1-1 to 1-10

First, comparison patches were obtained in the same manner as that of Example 1 except that adhesive agents of compositions shown in Tables 3 and 4 were used as adhesive agents. Next, the in vitro hairless mouse skin permeation test and the crystal precipitation evaluation test were conducted on the comparison patches obtained in Comparative Examples 1-1 to 1-10 in the same manner as that of Example 1 to evaluate the performances of the patches. Note that the results of the skin permeation test on the comparison patches of Comparative Examples 1-1 to 1-3 are shown in Table 5 and FIG. 1, and the results of the crystal precipitation evaluation test on the comparison patches of Comparative Examples 1-1 to 1-10 are shown in Table 6.

As is clear from the results shown in Tables 3 to 6 and FIG. 1, it was confirmed that in the patch of Example 1, the precipitation of crystals of butorphanol was sufficiently suppressed and the skin permeability of butorphanol was excellent. As shown above, it was confirmed that the non-cross-linking polyvinylpyrrolidone that does not contain vinyl acetate as the constituent monomer, which was used as the crystal precipitation inhibitor in Example 1, has little influence on (or did not lower) the skin permeability of the drug, and also is excellent in the effect of suppressing the precipitation of crystals of the drug.

Examples 2-1 to 2-5

First, patches according to Examples 2-1 to 2-5 were obtained in the same manner as that of Example 1 except that adhesive agents of compositions shown in Table 7 were used as adhesive agents.

Next, the in vitro hairless mouse skin permeation test and the crystal precipitation evaluation test were conducted on the patches obtained in Examples 2-1 to 2-5 as described below, to evaluate the performances of the patches.

<In Vitro Hairless Mouse Skin Permeation Test>

First, the skin of the trunk of a hairless mouse was peeled off, and the fat was removed from the skin. Next, the patch was attached to the epidermis side, and then set in a Franz permeation test cell of a flow-through type such that the dermis side came into contact with a receptor solution. Subsequently, the cell was filled with the receptor solution (PBS), and a circulation water, which had been warmed such that the solution was kept at a temperature of 32° C., was circulated around the outer periphery of the cell, and the receptor solution was fed at a flow rate of approximately 5 mL/hr or approximately 2.5 mL/hr. Then, the solution was collected every 2 hours for 20 hours, or every 4 hours for 24 hours. The concentration of butorphanol (salt) in the obtained solution was measured by high performance liquid chromatography, and the skin permeation amount (rate) of butorphanol (salt) per hour was calculated. The maximum value of the skin permeation rate was taken as Jmax. In addition, the accumulated permeation amount of the drug until 20 hours was calculated. Moreover, the rate of utilization (%) of the drug was calculated in accordance with the following equation:

The rate of utilization (%)={(the accumulated skin permeation amount of the drug for 24 hours per 1 cm² of the patch)/(the content of the drug per 1 cm² of the patch)}×100.

The preparation having a large value of the maximum value of skin permeation rate and/or the accumulated skin permeation amount is confirmed to be excellent in skin permeability of the drug.

<Crystal Precipitation Evaluation Test>

The prepared patch was packaged in an aluminum-laminate packaging material and stored in a chamber having a temperature of 40° C. and a humidity of 75%. After 1 month, the surface of the adhesive layer of the patch was visually observed to check whether the crystal precipitation had occurred.

Regarding the obtained patches, the compositions of the adhesive agents are shown in Table 7, the results of the conducted skin permeation test are shown in Table 8 and FIG. 2, and the results of the conducted crystal precipitation evaluation test are shown in Table 9.

TABLE 7

| Component | Example 2-1 | Example 2-2 | Example 2-3 | Example 2-4 | Example 2-5 |
|---|---|---|---|---|---|
| SIS Block Copolymer | 13.2 | 13.6 | 12.8 | 11.2 | 14.4 |
| PIB | 5.7 | 5.8 | 5.5 | 11.2 | 6.2 |
| Tackifier Resin | 34.1 | 35.1 | 33.1 | 25.9 | 37.0 |
| Liquid Paraffin | 15.1 | 15.6 | 14.7 | 13.8 | 16.5 |
| Butorphanol Tartrate | 9.0 | 9.0 | 9.0 | 9.0 | 9.0 |
| Anhydrous Sodium Acetate | 3.9 | 3.9 | 3.9 | 3.9 | 3.9 |
| Oleyl Alcohol | 10.0 | 10.0 | 10.0 | 10.0 | 10.0 |
| PVP K-30 | 9.0 | 7.0 | 11.0 | 15.0 | 3.0 |
| Total [% by mass] | 100.0 | 100.0 | 100.0 | 100.0 | 100.0 |

TABLE 8

| | Maximum Skin Permeation Rate (Jmax) [µg/cm²/hr] | Accumulated Skin Permeation Amount [µg/cm²/20 hr] | Rate of Utilization [%] |
|---|---|---|---|
| Example 2-1 | 32 | 420 | 47 |
| Example 2-2 | 30 | 402 | 45 |
| Example 2-3 | 27 | 362 | 40 |
| Example 2-4 | 32 | 430 | 48 |
| Example 2-5 | 27 | 389 | 43 |

TABLE 9

| | Crystal Precipitation (Visually Checked) |
|---|---|
| Example 2-1 | No |
| Example 2-2 | Crystals were Found Very Slightly at Edge of Patch |
| Example 2-3 | No |
| Example 2-4 | No |
| Example 2-5 | Crystals were Found Slightly at Edge of Patch |

As is clear from the results shown in Tables 7 to 9 and FIG. 2, it was confirmed that in the patches of Examples 2-1 to 2-5, the precipitation of crystals of butorphanol was sufficiently suppressed and the skin permeability of butorphanol was excellent. It was also confirmed that when the content of the polyvinylpyrrolidone used as the crystal precipitation inhibitor in Examples 2-1 to 2-5 is small, crystals of butorphanol (or a salt thereof) are likely to precipitate while when the content is large, PVP tends to be left undissolved in the patch. Note that the amount of crystals precipitated in Example 2-2 was about 10% of the adhesive-layer formed surface of the patch, and the amount of crystals precipitated in Example 2-5 was about 30% of the adhesive-layer formed surface of the patch. In addition, in these Examples, it was confirmed that when the content of butorphanol tartrate is 9% by mass, the optimum content of the polyvinylpyrrolidone is 9% by mass. It was confirmed from these examples that the content of the polyvinylpyrrolidone is preferably at a concentration of more than 3% by mass but 15% by mass or lower, based on the total mass of the adhesive layer.

Examples 3-1 to 3-3

First, patches according to Examples 3-1 to 3-3 were obtained in the same manner as that of Example 1 except that adhesive agents of compositions shown in Table 10 were used as adhesive agents.

Next, the in vitro hairless mouse skin permeation test and the crystal precipitation evaluation test were conducted on the patches obtained in Examples 3-1 to 3-3 in the same manner as that of Example 2, to evaluate the performances of the patches.

Regarding the obtained patches, the compositions of the adhesive agents are shown in Table 10, the results of the conducted skin permeation test are shown in Table 11 and FIG. 3, and the results of the conducted crystal precipitation evaluation test are shown in Table 12.

TABLE 10

| Component | Example 3-1 | Example 3-2 | Example 3-3 |
|---|---|---|---|
| SIS Block Copolymer | 13.2 | 13.5 | 13.7 |
| PIB | 5.7 | 5.8 | 5.9 |
| Petroleum-based Resin | 33.9 | 34.6 | 35.3 |
| Liquid Paraffin | 15.1 | 15.4 | 15.7 |
| Butorphanol Tartrate | 9.0 | 8.0 | 7.0 |
| Anhydrous Sodium Acetate | 3.1 | 2.7 | 2.4 |
| Oleyl Alcohol | 10.0 | 10.0 | 10.0 |
| PVP K-30 | 10.0 | 10.0 | 10.0 |
| Total [% by mass] | 100.0 | 100.0 | 100.0 |

TABLE 11

| | Maximum Skin Permeation Rate (Jmax) [μg/cm$^2$/hr] | Accumulated Skin Permeation Amount [μg/cm$^2$/20 hr] | Rate of Utilization [%] |
|---|---|---|---|
| Example 3-1 | 24 | 309 | 34 |
| Example 3-2 | 22 | 287 | 36 |
| Example 3-3 | 17 | 202 | 29 |

TABLE 12

| | Crystal Precipitation (Visually Checked) |
|---|---|
| Example 3-1 | No |
| Example 3-2 | No |
| Example 3-3 | No |

As is clear from the results shown in Tables 10 to 12 and FIG. 3, it was confirmed that in the patches of Examples 3-1 to 3-3, the precipitation of crystals of butorphanol was sufficiently suppressed and the skin permeability of butorphanol was excellent. It was also confirmed from the results of Examples 3-1 to 3-3 that when the content of butorphanol tartrate is 7% by mass, a sufficient permeability is obtained, and when the content is 9% by mass, the drug is most excellent in skin permeability.

Examples 4-1 to 4-3

First, patches according to Examples 4-1 to 4-3 were obtained in the same manner as that of Example 1 except that adhesive agents of compositions shown in Table 13 were used as adhesive agents.

Next, the crystal precipitation evaluation test was conducted on the patches obtained in Examples 4-1 to 4-3 in the same manner as that of Example 2, to evaluate the performances of the patches.

Regarding the obtained patches, the compositions of the adhesive agents are shown in Table 13, and the results of the conducted crystal precipitation evaluation test are shown in Table 14.

TABLE 13

| Component | Example 4-1 | Example 4-2 | Example 4-3 |
|---|---|---|---|
| DURO-TAK 87-2510 | 70.6 | — | — |
| DURO-TAK 87-900A | — | 70.6 | — |
| DURO-TAK 87-2194 | — | — | 70.6 |
| Butorphanol Tartrate | 7.0 | 7.0 | 7.0 |
| Anhydrous Sodium Acetate | 2.4 | 2.4 | 2.4 |
| Oleyl Alcohol | 10.0 | 10.0 | 10.0 |
| PVP K-30 | 10.0 | 10.0 | 10.0 |
| Total [% by mass] | 100.0 | 100.0 | 100.0 |

TABLE 14

| | Crystal Precipitation (Visually Checked) |
|---|---|
| Example 4-1 | No |
| Example 4-2 | No |
| Example 4-3 | No |

As is clear from the results shown in Tables 13 to 14, it was confirmed that even when acrylic adhesive base agents are used as the adhesive base agents of the patches of Examples 4-1 to 4-3, the precipitation of crystals of butorphanol is sufficiently suppressed.

INDUSTRIAL APPLICABILITY

As described above, according to the present invention, it is possible to provide a patch in which the precipitation of crystals of butorphanol is sufficiently suppressed and which is excellent in skin permeability of butorphanol.

The invention claimed is:

1. A patch, comprising:
a support; and
an adhesive layer disposed on at least one surface of the support,
wherein the adhesive layer comprises a higher aliphatic alcohol having 12 to 20 carbon atoms, a non-cross-linking polyvinylpyrrolidone that does not contain vinyl acetate as a constituent monomer, and at least one of butorphanol and a pharmaceutically acceptable salt thereof; wherein the content of the higher aliphatic alcohol is in a range of 3 to 25% by mass based on the total mass of the adhesive layer, the content of the butorphanol and/or pharmaceutically acceptable salt thereof is 4 to 20% by mass based on the total mass of the adhesive layer, the content of the non-cross-linking polyvinylpyrrolidone is in a range of 4 to 20% by mass based on the total mass of the adhesive layer, the non-cross-linking polyvinylpyrrolidone has a K value in a range of 10 to 30; and wherein precipitation of crystals derived from the butorphanol and/or pharmaceutically acceptable salt thereof is suppressed.

2. The patch according to claim 1, wherein the higher aliphatic alcohol is at least one selected from the group consisting of isostearyl alcohol, octyldodecanol, and oleyl alcohol.

3. The patch according to claim 1, wherein a content ratio between the butorphanol and/or pharmaceutically acceptable salt thereof and the non-cross-linking polyvinylpyrrolidone is in a range of 1:0.8 to 2.5 in mass ratio.

4. The patch according to claim 1, wherein the adhesive layer further comprises a styrene-isoprene-styrene block copolymer.

5. The patch according to claim 2, wherein a content ratio between the butorphanol and/or pharmaceutically acceptable salt thereof and the non-cross-linking polyvinylpyrrolidone is in a range of 1:0.8 to 2.5 in mass ratio.

6. The patch according to claim 2, wherein the adhesive layer further comprises a styrene-isoprene-styrene block copolymer.

7. The patch according to claim 3, wherein the adhesive layer further comprises a styrene-isoprene-styrene block copolymer.

8. The patch according to claim 5, wherein the adhesive layer further comprises a styrene-isoprene-styrene block copolymer.

9. The patch according to claim 1, wherein the content of the higher aliphatic alcohol is in a range of 3 to 5% by mass based on the total mass of the adhesive layer.

* * * * *